United States Patent
Huang et al.

(10) Patent No.: US 9,872,622 B2
(45) Date of Patent: Jan. 23, 2018

(54) MAGNETIC RESONANCE THERMOGRAPHY: HIGH RESOLUTION IMAGING FOR THERMAL ABNORMALITIES

(71) Applicant: KONINKLIJKE PHILIPS N.V., Eindhoven (NL)

(72) Inventors: Feng Huang, Gainesville, FL (US); Arne Reykowski, Gainesville, FL (US); George Randall Duensing, Gainesville, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 866 days.

(21) Appl. No.: 14/368,306

(22) PCT Filed: Dec. 13, 2012

(86) PCT No.: PCT/IB2012/057260
§ 371 (c)(1),
(2) Date: Jun. 24, 2014

(87) PCT Pub. No.: WO2013/098690
PCT Pub. Date: Jul. 4, 2013

(65) Prior Publication Data
US 2014/0309519 A1    Oct. 16, 2014

Related U.S. Application Data

(60) Provisional application No. 61/580,412, filed on Dec. 27, 2011.

(51) Int. Cl.
*A61B 5/05*    (2006.01)
*A61B 5/01*    (2006.01)
(Continued)

(52) U.S. Cl.
CPC .............. *A61B 5/01* (2013.01); *A61B 5/015* (2013.01); *A61B 5/055* (2013.01); *A61B 5/7275* (2013.01);
(Continued)

(58) Field of Classification Search
CPC ........... A61B 5/015; A61B 5/05; A61B 5/055; A61B 5/01; A61B 5/1048; A61B 5/742; A61B 5/7275
See application file for complete search history.

(56) References Cited

U.S. PATENT DOCUMENTS

| 5,916,161 A | 6/1999 | Ishihara |
| 8,598,879 B2 * | 12/2013 | Sakakura ............... A61B 5/015 324/315 |

(Continued)

FOREIGN PATENT DOCUMENTS

| CA | 2757358 A1 | 12/2001 |
| CN | 101352342 A | 1/2009 |

(Continued)

OTHER PUBLICATIONS

Shmatukha, Andriy V. et al "MRI Temperature Mapping During Thermal Balloon Angioplasty", Physics in Medicine and Biology, vol. 51, 2006, pp. 11-19.

*Primary Examiner* — Joel Lamprecht

(57) ABSTRACT

A magnetic resonance scanner (12) is configured for thermographic imaging. One or more processors (28) receive (56) thermal image data from the magnetic resonance scanner and reconstruct at least one thermal image in which each voxel includes a measure of temperature change. The one or more processors identify (58) thermally abnormal voxels. A display (44) displays at least one reconstructed image with the identified abnormal thermal locations.

17 Claims, 4 Drawing Sheets

Figure 1:
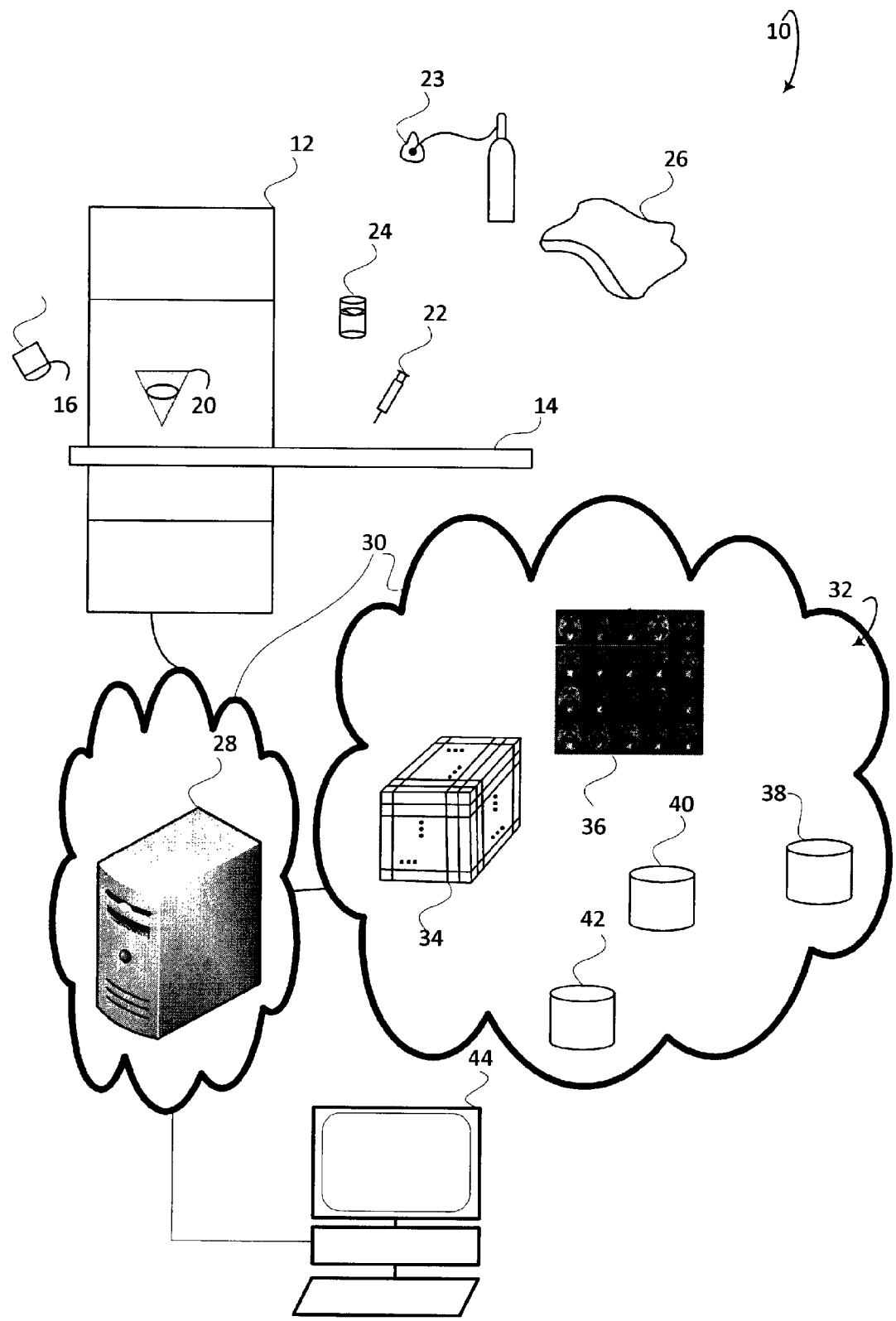

(51) Int. Cl.
  *A61B 5/055* (2006.01)
  *G01R 33/48* (2006.01)
  *A61B 5/00* (2006.01)
  *A61N 5/10* (2006.01)
  *A61N 7/02* (2006.01)

(52) U.S. Cl.
  CPC ............ *A61B 5/7282* (2013.01); *A61B 5/742* (2013.01); *A61N 5/1048* (2013.01); *A61N 7/02* (2013.01); *G01R 33/4804* (2013.01); *G01R 33/4808* (2013.01)

(56) References Cited

U.S. PATENT DOCUMENTS

| | | |
|---|---|---|
| 2008/0194941 A1 | 8/2008 | Steinmeyer et al. |
| 2009/0227859 A1 | 9/2009 | Pile-Spellman |
| 2011/0279116 A1 | 11/2011 | Sakakura |

FOREIGN PATENT DOCUMENTS

| | | |
|---|---|---|
| JP | 0880290 A | 3/1996 |
| WO | 2010140125 A1 | 12/2010 |

* cited by examiner

MAGNETIC RESONANCE THERMOGRAPHY: HIGH RESOLUTION IMAGING FOR THERMAL ABNORMALITIES

CROSS-REFERENCE TO PRIOR APPLICATIONS

This application is the U.S. National Phase application under 35 U.S.C. § 371 of International Application No. PCT/IB2012/057260, filed on Dec. 13, 2012, which claims the benefit of U.S. Provisional Patent Application No. 61/580,412, filed on Dec. 27, 2011. These applications are hereby incorporated by reference herein.

The present application relates generally to medical imaging. It finds particular application in conjunction with magnetic resonance imaging, and will be described with particular reference thereto. However, it will be understood that it also finds application in other usage scenarios and is not necessarily limited to the aforementioned application.

Different diseases and/or injuries have been reported in the medical literature as exhibiting thermal properties. The diseases and/or injuries include Cancer, back injuries, breast disease, arthritis, inflammatory pain, nerve damage, vascular disease, digestive disorders, stroke screening etc. The thermal properties distinguish the diseased and/or injured tissue from normal tissue. For example, a tumor usually has more vascular circulation than normal tissue. Tissue which has more vascular circulation will cool more quickly than normal tissue when the body acts to restore homeostatic balance after heating. Similarly tissue which has more vascular circulation will heat more quickly than normal tissue when the body acts to restore homeostatic balance after cooling.

Measuring temperatures of diseased or injured tissue is typically done through surface measurements. One technique is Digitial Infrared Thermal Imaging (DITI) which has been used since the 1980s. However, DITI can detect temperature changes only near the skin and not throughout the body. Magnetic resonance thermal imaging is the only currently known technique which is capable of measuring internal body temperatures without invasive procedures.

The present application discloses a new and improved Magnetic Resonance (MR) thermal imaging diagnostic method which addresses the above referenced matters, and others.

In accordance with one aspect, a magnetic resonance system includes a magnetic resonance scanner, one or more processors, and a display. The magnetic resonance scanner is configured for themographic measurement. The one or more processors receive thermal image data from the magnetic resonance scanner and reconstruct at least one image in which each voxel of a region of interest includes a measure of temperature change. The one or more processors identifies thermally abnormal voxels. The display displays the at least one reconstructed thermal image with the identified thermally abnormal voxels.

In accordance with another aspect, a method of magnetic resonance thermography receives thermal image data from a magnetic resonance scanner and reconstructs at least one thermal image in which each voxel in a region of interest indicates temperature change. Thermally abnormal voxels are identified in the at least one thermal image.

One advantage resides in non-invasiveness of thermal imaging of interior portions of the subject.

Another advantage resides in the accuracy of magnetic resonance thermal imaging to measure abnormal thermal properties.

Another advantage resides in safe methods for heating or cooling target areas of the body.

Another advantage resides in using thermal information for more accurate diagnosis.

Another advantage resides in monitoring the effectiveness of radiation therapies.

Another advantage resides in combination with developing, updating, or refining radiation therapy plans.

Still further advantages of the present application will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of a magnetic resonance scanner system with various devices for heating/cooling target areas of the subject body.

Figure 2:
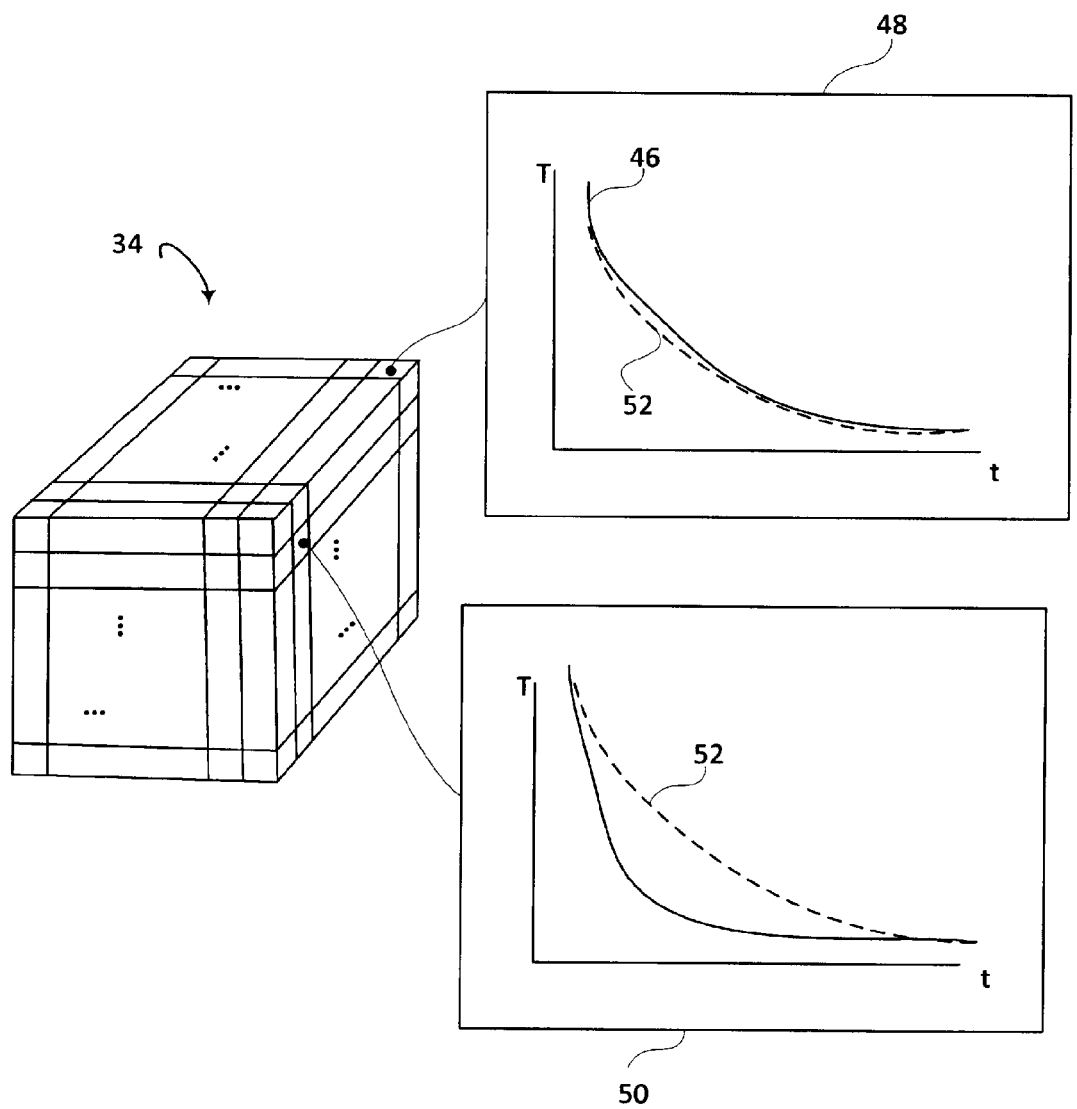

FIG. 2 schematically illustrates an example of one embodiment of a imaging volume and different voxel temperature (T) vs time (t) measurements.

Figure 3:
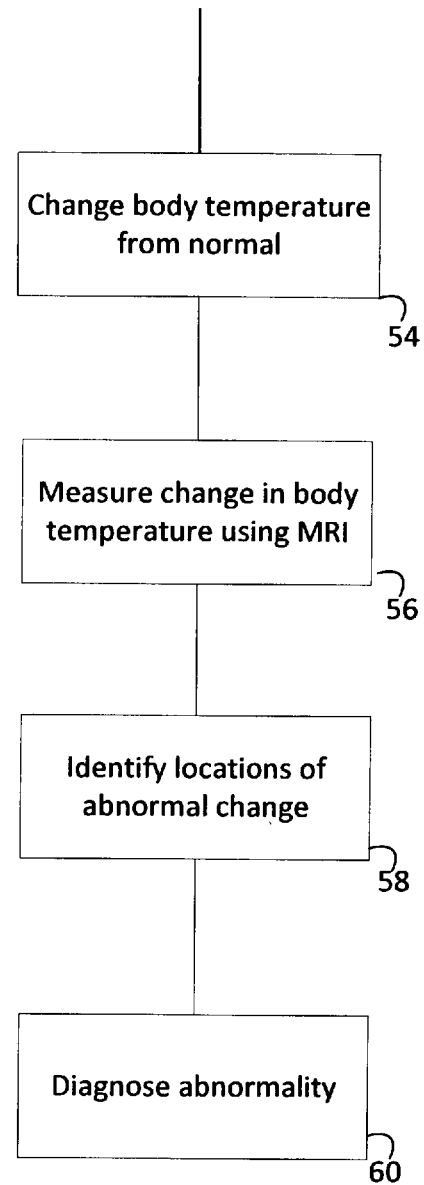

FIG. 3 flowcharts an embodiment of the method for diagnostic identifying thermal abnormalities.

Figure 4:
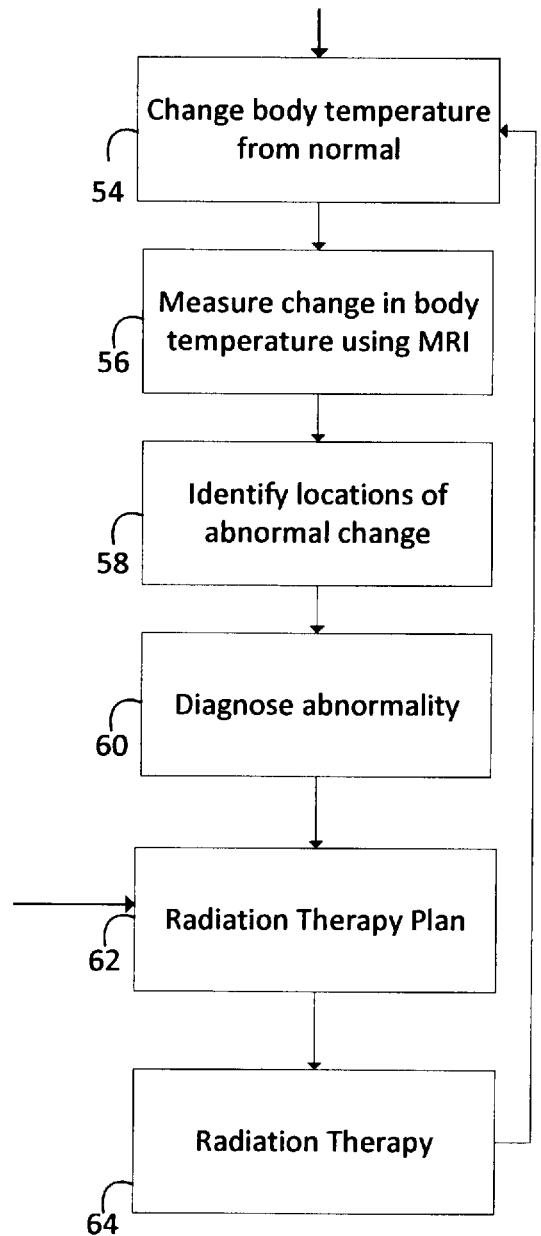

FIG. 4 flowcharts an embodiment of the system using in combination with radiation therapy planning.

With reference to FIG. 1, an embodiment of a magnetic resonance scanner system 10 with various devices for heating/cooling target areas of the subject body is schematically illustrated. A magnetic resonance (MR) scanner 12 is configured to generate magnetic resonance images indicative of the temperature of each voxel of a region of interest of the body. The MR scanner 12 is shown in a cross section with a patient support 14. MR scanners detect temperature changes as small as 0.1° C. Temperature changes to the body can be induced using a variety of techniques such as ultrasound, radio frequency (RF) pulses, ingested liquids, injected solutions, compresses, etc. The temperature changes are caused by a variety of devices such as a ultrasound emitter 16, a RF emitter 20, a syringe of thermal/chemical solution 22, a vessel of thermal/chemical liquid to be consumed by the patient 24, a mask connected to a gas which is inhaled by a patient 25, a hot/cold compress 26, etc. Temperature changes can also be natural such as due to exercise active or passive, and natural body temperature cycles which occur daily.

Thermal imaging data from the MR scanner 12 is transmitted to one or more processors 28 via a network 30. The processors can contain transitory and non-transitory memory. The network 30 includes a wired or wireless connection, a direct connect, or by a network connection such as a private network or the Internet. The processors can be contained within one server or across multiple servers.

A data storage 32 is attached to the one or more processors with a variety of different connection options. The data storage can be directly attached individual volumes, network attached storage, and the like. The data storage 32 provides storage for the received thermal imaging data 34, stored collectives of thermal images 36, diagnostic databases 38, and databases of radiation therapy plans 40 and treatment methods 42. The stored collectives of thermal images include images which represent a defined population. The defined population can be a normal population, which includes thermal images of normal images that voxel by voxel represent the variation of normal changes in temperature for healthy individuals. The normal collective can be compared with the thermal image voxel by voxel after registering to a common space and a probability that each thermal image voxel is different calculated. Alternatively, the collective can represent a diseased population(s) such as those with a vascular disease of the brain. The thermal image can be compared with the collective to determine a probability that a voxel is similar to those found in the collective such as having vascular disease of the brain.

The diagnostic database includes diagnoses such as ICD-10, ICD-0, SNOMED, and the like. The diagnostic database includes morphology information and abnormal temperature change information. The diagnostic database enables cross reference of thermal abnormalities and possible diagnoses. The database of radiation therapy plans includes the steps and alternatives for treating a diagnosed condition. The treatment methods database includes parameters such as dosage and frequency of possible radiation therapies for diagnosed tumors, etc. The database of radiation therapy plans can extend beyond only magnetic resonance scanners, and include data concerning other devices typically used in conjunction or combination with magnetic resonance scanners such as HIghly Focused Ultrasound (HIFU), LINear Accelerator (LINAC), X-ray and the like.

A display device 44 is connected to the network 30 and to the one or more processors. The display device 44 allows the healthcare practitioner to interact with the system. The display device can be a computer, laptop, tablet, mobile device, and the like. The display device displays the images, possible diagnoses, radiation therapy plans, image comparisons, and the like. For example, the thermal image of a back depicting the change in temperature in the daily temperature cycle is displayed. The magnitude in change in temperature at each voxel is displayed as a color based intensity. The intensity can be normalized using the collective and a back injury indicated by the voxels which deviate significantly from the normative population. Alternatively, the intensity can be normalized using the temperature of the pulmonary artery as a reference region where each voxel is the difference between the temperature at the voxel and the temperature of the pulmonary artery. The intensity of the voxel can be represented as an average of the difference, a minimum, a maximum or some function which includes the temperature of the reference region, and the change overtime. Other internal organs and regions are also contemplated. The display device 44 also inputs commands and permits the health practitioner to direct the use of the imaging system.

FIG. 2 schematically illustrates an example of one embodiment of a imaging volume and different voxel temperature measurements. The thermal imaging data 34 is shown as an example volume of voxels represented as a 3 dimensional rectangular volume. The volume of voxels can be any shape or dimension. Each voxel is repeatedly imaged over time to generate a temperature change overtime measurement either as a continuous measurement or discrete measurements using sampling techniques. For example, temperature measurements can be continuous based on the magnetic resonance imaging data as it becomes available from the scanner during the heating or cooling of the target area. Another example, temperature changes from the magnetic resonance scanner are measured at 1 minute or 10 minute intervals. An additional example, temperature changes are taken at morning, noon, and evening to compare daily temperature cycles. Analytics can be applied which fit functions to measurements in each such as curve fitting, discrete statistics, and the like. For example, as the number of sample points increase, regression techniques can be applied to fit a curve. Alternative examples include model curves based upon normal tissue temperature change which are adapted or modified as data points are obtained. The model curve can be a declining parabolic function for a decreasing temperature where the magnitude of the bend is adjusted to the sample points. Curve fitting includes moving averages, linear regression, and the like. Discrete statistics includes threshold, minimum, maximum, average, according to various distributions such as normal, Poisson, etc., and the like. The temperature change measurements can be increasing or decreasing depending upon whether heat or cold sources are applied to initially change the body temperature before measuring the temperature change as the body restores homeostatic balance. For example, the heat source such as less focused HIFU is initially applied to breast tissue to warm the tissue several degrees. The heat source is removed and the body cools the breast tissue. Tumors present in the breast tissue have greater vascular circulation and will show a steeper cooling curve. The increased blood circulated to the diseased tissue cools the diseased tissue more quickly. In the example measurements, the temperature change 46 is represented as a solid line curve or continuous measurement. The solid line curve can be based on sampling technique and curve fitting techniques described previously. The graph of one voxel temperature measurement illustrates a decreasing temperature which is normal 48 while another voxel illustrates an abnormal or more rapidly decreasing temperature 50. In the example graphs, the more rapidly decreasing temperature curve is indicative of diseased tissue such as breast cancer.

The dotted line in the example graphs for two voxels are the expected temperature changes 52 for healthy tissue. The expected temperature changes 52 can be based on a variety of sources such as the collective 36, a reference area of the patient, a baseline of the patient, an adjacent region of the patient, etc. Different parts of the body will change temperature at different rates. For example, tissue and organs in the torso will cool or heat more rapidly than extremities. The collective represents the variability of normal among a population, but does not represent normal for an individual patient. The reference area of the patient such as the pulmonary artery represents normal for the patient, but does not account for the variability between the different tissues or the impact of diseased tissue. The baseline for the patient can be where the patient has been a rest before heating or cooling of a target area. The baseline can alternatively be a temperature change curve of a region different from the region of interest. For example, a cold compress can be applied to a leg, removed, and the temperature change curve developed for voxels within the leg. A model change curve can be constructed using the temperature change curve from the voxels of the leg and applied as a baseline for temperature change curve measured for a different region of interest such as the breast. The baseline can be a function of an anatomical feature such as the brain, heart, etc., an average of the voxels of a target area, the body at rest responding to an artificial heat source before exercising and measuring the temperature change in comparison, and the like.

The measured temperature change 46 is compared with the expected temperature change 52 and the difference can be represented as a probability of an abnormality. The difference can be measured as the area between the dotting line curve and the solid line curve in the example. Alternatively, a maximum rate change of each curve can be measured and compared for a threshold value indicative of an abnormal thermal voxel. Various techniques can be applied to determine the likihood of a difference between an expected and a measured temperature change. A probability map is developed which includes the probability of a presence of an abnormality for each voxel. In another embodiment, the thermal curve of each voxel is compared with a series of curves, each curve associated with a diagnosis, e.g. a normal curve, a cancer curve, curves for different stages or types of cancer, arthritis, strains, inflamation and the like.

In FIG. 3 an embodiment of the method for diagnostic identification based on thermal thermal abnormalities is flowcharted. In a first step 54, the body temperature is changed from normal or a baseline. The change can occur before or during the MR imaging sequence. Various devices as shown in reference to FIG. 1 can be used to elevate or decrease the body temperature of a target area. The body temperature can be elevated using active or passive exercise, natural body temperature daily cycles, and the like. The temperature of the target areas can typically safely increase 2-3° C. or decrease about 5° C. from normal which is easily sensed by MR thermography. For example, HIFU, which is used to kill diseased tissue internally in radiation therapy, can be less focused and used to heat the region of interest a few degrees. The magnetic resonance which is used to monitor HIFU therapies can also monitor the heating of a region of interest by HIFU for diagnositic purposes. Alternatively, if the digestive track includes the region of interest for example, then the patient can consume hot or cold water to heat or cool the digestive track. The liquid can be chemical based which temporarily elevates the body temperature as the chemical is absorbed. In another example, a saline solution can be injected which temporarily decreases the temperature of the blood. In another example, a cold gas can be inhaled which temporarily decreases the temperature of the pulmonary region. The gas can be thermally different to cause the thermal decrease or chemically based which cause the capillaries to dialate and lose heat during exhalation. In another example, exercise can raise the temperature of a region of interest through heat generated by muscle activity. Active patient exercise is exercise by the patient, wherein passive exercise is movement caused by another such as a physical therapist or electrical stimulation. Whatever form of exercise employed, muscle movement generates heat and the body will through homeostatis reduce the heat. Measuring the reduction in heat can be done easier when the body is at rest such as during imaging, and the cooling of muscle tissue produces measurable temperature changes.

The MR scanner measures the temperature changes in a step 56 as the body restores homoestatic balance, e.g. measures temperature repeatedly and generates a plot of temperature (T) vs time (t). The temperature can be measured with a thermal resolution of about 0.1° C. The measurement of temperature change was described in reference to FIG. 2. A probability map is developed in a step 58 which identifies a probability of abnormality at each voxel location. The locations including mapping to anatomical structures and/or regions of interest. The thermal curves can also be compared to reference thermal curves to determine a probability of a specific abnormality. For example, if maximum rate of temperature change for normal tissue is 0.3° C./min and the maximum rate of the thermal curve is 0.8° C./min, then there is a high probability that abnormal thermal tissue is present. The development of the probability map was described in reference to FIG. 2.

The mapped abnormal locations are correlated with possible diagnoses using the diagnoses database in a step 60. Other sources can be used such as other patient medical tests, other patient images, and the like. For example, blood test indicating presence of certain types of tumors, x-ray images show arthritis, etc. The possible diagnoses can be displayed to the healthcare practitioner with the MR images. The MR images can include the probability map of abnormal locations represented as different intensities. For example, voxels with high probabilities (e.g. >0.9) of thermal abnormalities can be shown in red, lower probabilities (e.g. >0.5) shown in yellow, etc.

The flowcharted embodiment uses a non-invasive method of MR thermagraphy which identifies temperature abnormalities. The identified temperature abnormalities are used to identify possible diagnoses, or to provide information which can be correlated with other diagnostic tools and techniques.

In FIG. 4 an embodiment of the system and method used in combination with radiation therapy planning is flowcharted. The embodiment described in reference to FIG. 3 can be used to identify abnormalities. Other sources can be used and the system used to monitor the progress of a patient response to a radiation therapy. Thus, a radiation therapy plan can be generated in a step 62 or a next step in a progressive cycle of radiation therapy planning The radiation therapy plan includes the initial size and location of a disease such as a tumor. The radiation therapy plan determines the manner and dose of radiation therapy such as with LINAC, HIFU, x-ray, and the like which is applied in a step 64. After radiation therapy is applied, the system measures the thermal temperature curve or change in the remaining target tissue, e.g. tumor. Changes in the thermal curve can be indicative of the relative success in killing tumor cells in each voxel. The system revises, updates, or refines the plan in accordance with the tumor destruction/survival as determined from the thermal curves.

It is to be appreciated that in connection with the particular exemplary embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

The invention claimed is:

1. A magnetic resonance system, comprising:
a thermal source configured to one of heat a region of interest or cool the region of interest relative to a baseline temperature;
a magnetic resonance scanner configured to generate thermographic data from the region of interest;
a diagnostic database configured to store at least one preselected temperature change curve characteristic;
one or more processors configured to:
receive the thermographic data from the magnetic resonance scanner and construct a thermal change curve for each voxel of the region of interest during a period of time when the temperature of the region of interest is returning toward the baseline temperature; and
compares characteristics of the constructed temperature change curve with the at least one stored temperature change curve characteristic to identify thermally abnormal voxels;
a display device configured to display at least one reconstructed image with the thermally abnormal voxels identified.

2. The magnetic resonance system according to claim 1, wherein the diagnostic database further stores at least one normal temperature change curve and wherein the one or more processors is further configured to:
compare each constructed temperature change curve with the at least one normal temperature change curve, wherein a greater a difference between the constructed and normal thermal change curves a higher a probability the tissue of the corresponding voxel is abnormal;
reconstruct a probability image in which values of each voxel are indicative of a probability of abnormality; and
control the display to display the probability image.

3. The magnetic resonance system according to claim 1, wherein the one or more processors are further configured to:
repeatedly reconstruct thermal images of the region of interest over time; and
construct the thermal change curves from the thermal images.

4. The magnetic resonance system according to claim 1 further including:
at least one collective of thermal change curves characteristics which represents a normative population; and
wherein the one or more processors are further configured to:
compare the thermal change curve characteristics of each voxel of the at least one constructed thermal change curve characteristics with the collective to identify potential diagnoses.

5. The magnetic resonance system according to claim 1, wherein the diagnostic database links possible diagnoses with thermal abnormalities.

6. The magnetic resonance system according to claim 1, wherein the thermal source includes an ultrasound emitter.

7. The magnetic resonance system according to claim 1, wherein the thermal source includes at least one of the following:
an injected chemical solution;
an inhaled gas;
an injected thermal/chemical liquid; and
an externally applied cold source.

8. A method of magnetic resonance thermography, comprising, with one or more processors:
receiving thermal image data form a magnetic resonance scanner and reconstructing thermal images in which values of each voxel in a region of interest of a patient indicates temperature change over time;
constructing a thermal change curve for each voxel of the region of interest during a period of time when the temperature of the region of interest is returning toward the baseline temperature;
comparing characteristics of the constructed temperature change curve for each voxel with the at least one stored temperature change curve characteristic to identify thermally abornal voxels;
reconstructing an image of the patient in which thermally abnormal voxels are identified; and
controlling a display device to display the image in which the thermally abnormal images are identified.

9. The method of magnetic resonance thermography according to claim 8, wherein the region of interest temperature change occurs by using at least one of:
an ultrasound emitter;
an externally applied thermal source;
an inhaled gas;
an injected thermal/chemical solution; and
an injected thermal/chemical liquid.

10. The method of magnetic resonance thermography according to claim 8, wherein identifying the thermally abnormal voxels includes:
comparing the temperature change over time in the voxels of the region of interest of the thermal images with expected temperature changes over time, wherein a greater a difference between the thermal image and expected temperature changes over time, a greater a probability of abnormality and wherein voxels of the reconstructed image are indicative of a probability of abnormality.

11. The method of magnetic resonance thermography according to claim 8, wherein the expected change is a function of at least one of:
an average of a volume, region, or anatomical segment of the region of interest;
a volume, region, or anatomical segment of the region of interest of a normative patient or patient collective;
a volume, region, or anatomical segment in a region of interest for a baseline of an imaged patient.

12. The method of magnetic resonance thermography according to claim 8, further including:
inputting the voxels of identified temperature change abnormalities to a radiation therapy plan; and
assessing an effect of a radiation therapy based on the presence of temperature change abnormalities.

13. A non-transitory computer-readable medium encoded to control one or more processors to perform according to claim 8.

14. A magnetic resonance system for diagnosing thermally abnormal voxels of a patient, the system comprising:
a diagnostic database configured to store temperature change over time curve characteristics indicative of normal tissue;

one or more processors configured to:
receive magnetic resonance data from voxels of a region of interest as a temperature of the region of interest returns toward a baseline temperature from one of an elevated temperature or a decreased temperature,
determine temperature changed over time curves for the voxels of the region of interest from the received magnetic resonance data,
compare characteristics of the determined temperature change over time curves with the temperature change curve characteristics stored in the diagnostic database to determine abnormal tissue,
reconstruct a diagnostic image in which the voxels corresponding to the abnormal tissue are identified; and
a display device configured to display the diagnostic image.

15. The magnetic resonance system according to claim 14, wherein the diagnostic database further stores temperature change over time curve characteristics indicative of each of a plurality of abnormal tissues and wherein the one or more processors are further configured to:
generate one or more potential diagnoses for the abnormal tissue based on comparing the determined temperature change over time curve characteristics with the temperature change over time curve characteristics stored in the diagnostic database.

16. The magnetic resonance system according to claim 14, wherein:
the one or more processors are further configured to determine a probability of abnormality for each voxel of the diagnostic image by comparing the determined and normal temperature change curve characteristics; and
the display device is configured to display the diagnostic image with the probability of abnormality of the voxels identified.

17. The magnetic resonance system according to claim 14, wherein the characteristic of the temperature change over time curves is a maximum rate of change.

* * * * *